(12) United States Patent
Chun et al.

(10) Patent No.: US 7,754,699 B2
(45) Date of Patent: Jul. 13, 2010

(54) ANTIVIRAL NUCLEOSIDES

(75) Inventors: Byoung-Kwon Chun, Robbinsville, NJ (US); Jeremy Clark, Birmingham, AL (US); Keshab Sarma, Sunnyvale, CA (US); Peiyuan Wang, Glen Rock, NJ (US)

(73) Assignee: Roche Palo Alto LLC, Palo Alto, CA (US)

( * ) Notice: Subject to any disclaimer, the term of this patent is extended or adjusted under 35 U.S.C. 154(b) by 691 days.

(21) Appl. No.: 11/635,898

(22) Filed: Dec. 8, 2006
(Under 37 CFR 1.47)

(65) Prior Publication Data
US 2007/0197463 A1    Aug. 23, 2007

Related U.S. Application Data

(60) Provisional application No. 60/749,319, filed on Dec. 9, 2005.

(51) Int. Cl.
- *A01N 43/04* (2006.01)
- *A61K 31/70* (2006.01)
- *C07H 19/00* (2006.01)
- *C07H 19/06* (2006.01)
- *C08B 37/00* (2006.01)

(52) U.S. Cl. .................. 514/49; 536/28.1; 536/28.4; 536/28.5; 536/124

(58) Field of Classification Search .......... None
See application file for complete search history.

(56) References Cited

U.S. PATENT DOCUMENTS

| | | | |
|---|---|---|---|
| 6,348,587 B1 | 2/2002 | Schinazi et al. | |
| 6,846,810 B2 | 1/2005 | Martin et al. | |
| 6,911,424 B2 | 6/2005 | Schinazi et al. | |
| 7,105,499 B2 | 9/2006 | Carroll et al. | |
| 7,268,119 B2 * | 9/2007 | Cook et al. | 514/43 |
| 7,608,600 B2 | 10/2009 | Storer et al. | |
| 2005/0009737 A1 | 1/2005 | Clark | |

FOREIGN PATENT DOCUMENTS

| | | | |
|---|---|---|---|
| WO | WO 99/43691 A1 | 9/1999 | |
| WO | WO 01/09121 A2 | 2/2001 | |
| WO | WO 01/09121 A3 | 2/2001 | |
| WO | WO 01/90121 A2 | 11/2001 | |
| WO | WO 01/90121 A3 | 11/2001 | |
| WO | WO 01/92282 A2 | 12/2001 | |
| WO | WO 01/92282 A3 | 12/2001 | |
| WO | WO 02/057287 A2 | 7/2002 | |
| WO | WO 02/057287 A3 | 7/2002 | |
| WO | WO 02/057425 A2 | 7/2002 | |
| WO | WO 02/057425 A3 | 7/2002 | |
| WO | WO 03/026589 A2 | 4/2003 | |
| WO | WO 03/026589 A3 | 4/2003 | |
| WO | WO 2004/002422 A2 | 1/2004 | |
| WO | WO 2004/002422 A3 | 1/2004 | |
| WO | WO 2004/002999 A2 | 1/2004 | |
| WO | WO 2004/046331 A2 | 6/2004 | |
| WO | WO2005/003147 | * | 1/2005 |
| WO | WO 2005/003147 A2 | 1/2005 | |
| WO | WO 2005/009418 A2 | 2/2005 | |
| WO | WO 2005/009418 A3 | 2/2005 | |

OTHER PUBLICATIONS

Pogam et al., "No Evidence of R7128 Drug Resistance After Up to 4 Weeks Treatment of GT1,2 and 3 Hepatitis C Virus Infected Individuals", From 44th Annual Meeting of the European Association for the Study of the Liver (EASL), Copenhagen, Denmark Apr. 22-Apr. 26, 2009.*

Sofia et al., "R7128, A Potent and Selective Nucleoside Inhibitor of HCV NS5B Polymerase: An Overview of Clinical Efficacy and Progress Toward Second Generation Inhibitors", From HCV Drug Discovery 2008, Chicago, IL, Apr. 28, 2008.*

Jeremy L. Clark et al., Design, Synthesis and Antiviral Avtivity of 2'-Deoxy-2'-fluoro-2'-C-methylcytidine, a potent inhibitor of HCV Replication, *J. Med. Chem.* 2005 48(17):5504-5508.

C. Pierra et al., Synthesis and Pharmacokinetics of Valopicitabine (NM283), an Efficient Prodrug of the Potent Anti-HCV Agent 2'-C-Methylcytidine, *J. Med Chem.* 2006 49(22):6614-6620.

* cited by examiner

*Primary Examiner*—Traviss C McIntosh, III
(74) *Attorney, Agent, or Firm*—Brian L. Buckwalter

(57) ABSTRACT

Compounds having the formula I wherein $R^1$ is as herein defined are Hepatitis C virus NS5b polymerase inhibitors. Also disclosed are compositions and methods for inhibiting hepatitis replication, and processes for making the compounds of formula I

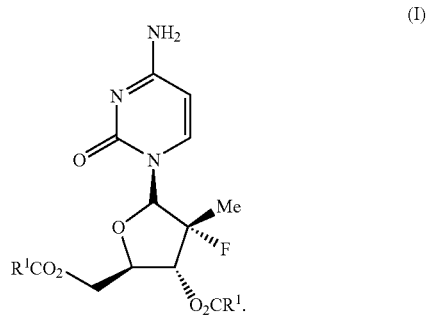

(I)

16 Claims, No Drawings

ANTIVIRAL NUCLEOSIDES

CROSS REFERENCE TO PRIOR APPLICATIONS

This application claims the benefit of priority to U.S. Ser. No. 60/749,319 filed Dec. 9, 2005 the contents of which are hereby incorporated in their entirety by reference

STATEMENT OF JOINT RESEARCH

This invention was made pursuant to a joint research agreement between Pharmasset, Inc. and Hoffmann-LaRoche Inc.

FIELD OF THE INVENTION

The present invention provides acylated nucleosides which are prodrugs of an inhibitor of Hepatitis C Virus (HCV) RNA-dependent RNA viral polymerase. These compounds when administered orally are readily absorbed from the GI tract and efficiently revert to the parent nucleoside in the blood. These prodrugs are inhibitors of RNA-dependent RNA viral replication and are useful as inhibitors of HCV NS5B polymerase, as inhibitors of HCV replication, and for the treatment of hepatitis C infection in mammals.

BACKGROUND

The invention relates nucleoside prodrugs which are inhibitors of HCV replication. In particular, the invention is concerned with the use of acylated pyrimidine nucleoside compounds which provide improved drug absorption when the nucleoside is administered orally.

Hepatitis C virus is a major health problem and the leading cause of chronic liver disease throughout the world. (Boyer, N. et al. *J. Hepatol.* 2000 32:98-112). Patients infected with HCV are at risk of developing cirrhosis of the liver and subsequent hepatocellular carcinoma and, hence, HCV is the major indication for liver transplantation.

According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit as resistance develops rapidly. There is an urgent need for improved therapeutic agents that effectively combat chronic HCV infection HCV has been classified as a member of the virus family Flaviviridae that includes the genera flaviviruses, pestiviruses, and hepaciviruses which includes hepatitis C viruses (Rice, C. M., Flaviviridae: The viruses and their replication, in: *Fields Virology*, Editors: Fields, B. N., Knipe, D. M., and Howley, P. M., Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5'-untranslated region (UTR), a long open reading frame (ORF) encoding a polyprotein precursor of approximately 3011 amino acids, and a short 3' UTR. The 5' UTR is the most highly conserved part of the HCV genome and is important for the initiation and control of polyprotein translation.

Genetic analysis of HCV has identified six main genotypes showing a >30% divergence in their DNA sequence. Each genotype contains a series of more closely related subtypes which show a 20-25% divergence in nucleotide sequences (Simmonds, P. 2004 *J. Gen. Virol.* 85:3173-88). More than 30 subtypes have been distinguished. In the US approximately 70% of infected individuals have Type 1a and 1b infection. Type 1b is the most prevalent subtype in Asia. (X. Forns and J. Bukh, *Clinics in Liver Disease* 1999 3:693-716; J. Bukh et al., *Semin. Liv. Dis.* 1995 15:41-63). Unfortunately Type 1 infections are more resistant to therapy than either the type 2 or 3 genotypes (N. N. Zein, *Clin. Microbiol. Rev.*, 2000 13:223-235).

The genetic organization and polyprotein processing of the nonstructural protein portion of the ORF of pestiviruses and hepaciviruses is very similar. These positive stranded RNA viruses possess a single large ORF encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al. *Nature* 1988 333:22; Bazan and Fletterick *Virology* 1989 171:637-639; Gorbalenya et al. *Nucleic Acid Res.* 1989 17.3889-3897). Similarly, the NS5B proteins of pestiviruses and hepaciviruses have the motifs characteristic of RNA-directed RNA polymerases (Koonin, E. V. and Doija, V. V. *Crit. Rev. Biochem. Molec. Biol.* 1993 28:375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett *Virology* 1991 184:341-350; Bartenschlager et al. *J. Virol.* 1993 67:3835-3844; Eckart et al. *Biochem. Biophys. Res. Comm.* 1993 192:399-406; Grakoui et al. *J. Virol.* 1993 67:2832-2843; Grakoui et al. *Proc. Natl. Acad. Sci. USA* 1993 90:10583-10587; Ilijikata et al. *J. Virol.* 1993 67:4665-4675; Tome et al. *J. Virol.* 1993 67:4017-4026). The NS4A protein, in both cases, acts as a cofactor with the NS3 serine protease (Bartenschlager et al. *J. Virol.* 1994 68:5045-5055; Failla et al. *J. Virol.* 1994 68: 3753-3760; Xu et al. *J Virol.* 1997 71:53 12-5322). The NS3 protein of both viruses also functions as a helicase (Kim et al. *Biochem. Biophys. Res. Comm.* 1995 215: 160-166; Jin and Peterson *Arch. Biochem. Biophys.* 1995, 323:47-53; Warrener and Collett *J. Virol.* 1995 69:1720-1726). Finally, the NS5B proteins of pestiviruses and hepaciviruses have the predicted RNA-directed RNA polymerases activity (Behrens et al. EMBO 1996 15:12-22; Lechmann et al. *J. Virol.* 1997 71:8416-8428; Yuan et al. *Biochem. Biophys. Res. Comm.* 1997 232:231-235; Hagedorn, PCT WO 97/12033; Zhong et al. *J. Virol.* 1998 72:9365-9369).

Currently there are a limited number of approved therapies are currently available for the treatment of HCV infection. New and existing therapeutic approaches to treating HCV and inhibition of HCV NS5B polymerase have been reviewed: R. G. Gish, *Sem. Liver. Dis.*, 1999 19:5; Di Besceglie, A. M. and Bacon, B. R., *Scientific American*, October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patents on experimental therapy for hepatitis C virus infection (1999-2002), *Exp. Opin. Ther. Patents* 2003 13(11):1707-1723; F. F. Poordad et al. Developments in Hepatitis C therapy during 2000-2002, *Exp. Opin. Emerging Drugs* 2003 8(1):9-25; M. P. Walker et al., Promising Candidates for the treatment of chronic hepatitis C, *Exp. Opin. Investig. Drugs* 2003 12(8): 1269-1280; S.-L. Tan et al., Hepatitis C Therapeutics: Current Status and Emerging Strategies, *Nature Rev. Drug Discov.* 2002 1:867-881; R. De Francesco et al. Approaching a new era for hepatitis C virus therapy: inhibitors of the NS3-4A serine protease and the NS5B RNA-dependent RNA polymerase, *Antiviral Res.* 2003 58:1-16; Q. M. Wang et al. Hepatitis C virus encoded proteins: targets for antiviral therapy, *Drugs of the Future* 2000 25(9):933-8-944; J. A. Wu and Z. Hong, Targeting NS5B-Dependent RNA Polymerase for Anti-HCV Chemotherapy *Cur. Drug Targ.-Inf. Dis.* 2003 3:207-219. The reviews cite compounds presently in various stages of the development process. Combination therapy with two or three agents directed to the same or different targets has become standard therapy to avoid or slow the development of resistant strains of a virus and the compounds disclosed in the above reviews could be used in combination therapy with compounds of the present invention and these reviews are hereby incorporated by reference in their entirety.

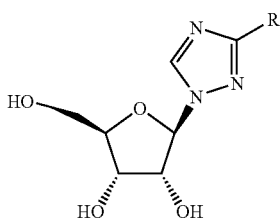

1a: R=C(=O)NH$_2$
1b: R=C(=NH$^+$)NH$_2$

Ribavirin (1a; 1-((2R,3R,4S,5R)-3,4-Dihydroxy-5-hydroxymethyl-tetrahydro-furan-2-yl)-1H-[1,2,4]triazole-3-carboxylic acid amide; VIRAZOLE®) is a synthetic, non-interferon-inducing, broad spectrum antiviral nucleoside analog. Ribavirin has in vitro activity against several DNA and RNA viruses including Flaviviridae (Gary L. Davis, *Gastroenterology* 2000 118:S104-S114). In monotherapy ribavirin reduces serum amino transferase levels to normal in 40% of patients, but it does not lower serum levels of HCV-RNA. Ribavirin also exhibits significant toxicity and is known to induce anemia. Ribavirin is an inhibitor of inosine monophosphate dehydrogenase. Ribovirin is not approved in monotherapy against HCV but the compound is approved in combination therapy with interferon α-2a and interferon α-2b. Viramidine 1b is a prodrug converted to 1a in hepatocytes.

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon β, type 2 includes interferon γ. Type 1 interferon is produced mainly by infected cells and protects neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (L.-B. Davis, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release,* 2001 72:217-224).

Interferon α-2a and interferon α-2b are currently approved as monotherapy for the treatment of HCV. ROFERON-A® (Roche) is the recombinant form of interferon α-2a. PEGASYS® (Roche) is the pegylated (i.e. polyethylene glycol modified) form of interferon α-2a. INTRON-A® (Schering Corporation) is the recombinant form of Interferon α-2b, and PEG-INTRON® (Schering Corporation) is the pegylated form of interferon α-2b.

Other forms of interferon α, as well as interferon β, γ, τ and ω are currently in clinical development for the treatment of HCV. For example, INFERGEN® (interferon alphacon-1) by InterMune, OMNIFERON® (natural interferon) by Viragen, ALBUFERON® by Human Genome Sciences, REBIF® (interferon β-1a) by Ares-Serono, Omega Interferon by BioMedicine, Oral Interferon Alpha by Amarillo Biosciences, and interferon γ, interferon τ, and interferon γ-1b by InterMune are in development.

Combination therapy of HCV with ribavirin and interferon-α currently represent the optimal therapy. Combining ribavirin and PEG-IFN (infra) results in a sustained viral response in 54-56% of patients. The SVR approaches 80% for type 2 and 3 HCV. (Walker, supra) Unfortunately, the combination also produces side effects which pose clinical challenges. Depression, flu-like symptoms and skin reactions are associated with subcutaneous IFN-α and hemolytic anemia is associated with sustained treatment with ribavirin.

Other macromolecular compounds currently in preclinical or clinical development for treatment of hepatitis C virus infection include: Interleukin-10 by Schering-Plough, IP-SO1 by Intemeuron, Merimebodib (VX-497) by Vertex, HEPTAZYME® by RPI, IDN-6556 by Idun Pharma., XTL-002 by XTL., HCV/MFS9 by Chiron, CIVACIR® (hepatitis C Immune Globulin) by NABI, ZADAXIN® (thymosin α-1) by SciClone, thymosin plus pegylated interferon by SciClone, CEPLENE®; a therapeutic vaccine directed to E2 by Innogenetics, therapeutic vaccine by Intercell, therapeutic vaccine by Epimmune/Genencor, a therapeutic vaccine by Merix, a therapeutic vaccine, Chron-VacC, by Tripep.

Other macromolecular approaches include ribozymes targeted at HCV RNA. Ribozymes are short naturally occurring molecules with endonuclease activity that catalyze the sequence-specific cleavage of RNA. An alternate approach is the use of antisense oligonucleotides bind to RNA and stimulate RNaseH mediated cleavage.

A number of potential molecular targets for drug development as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Nucleoside inhibitors of NS5B polymerase can act either as a non-natural substrate that results in chain termination or as a competitive inhibitor which competes with nucleotide binding to the polymerase. To function as a chain terminator the nucleoside analog must be taken up be the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. Unfortunately, this limits the direct evaluation of nucleosides as inhibitors of HCV replication to cell-based assays capable of in situ phosphorylation.

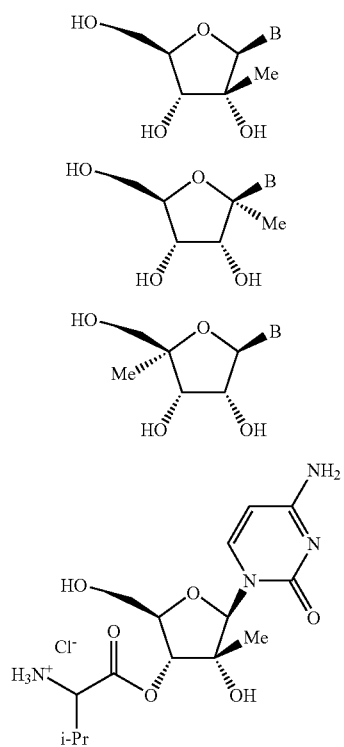

B=adenine, thymidine, uracil, cytidine, guanine and hypoxanthine

In WO 01 90121 published Nov. 29, 2001, J.-P. Sommadossi and P. Lacolla disclose and exemplify the anti-HCV polymerase activity of 1'-alkyl- and 2'-alkyl nucleosides of formulae 2 and 3. In WO 01/92282, published Dec. 6, 2001, J.-P. Sommadossi and P. Lacolla disclose and exemplify treating Flaviviruses and Pestiviruses with 1'-alkyl- and 2'-alkyl nucleosides of formulae 2 and 3. In WO 03/026675 published Apr. 3, 2003, G. Gosselin discloses 4'-alkyl nucleosides 4 for treating Flaviviruses and Pestiviruses.

In WO2004003000 published Jan. 8, 2004, J.-P. Sommadossi et al. disclose 2'- and 3' prodrugs of 1'-, 2'-, 3'- and 4'-substituted β-D and β-L nucleosides. In WO 2004/002422 published Jan. 8, 2004, 2'-C-methyl-3'-O-valine ester ribofuranosyl cytidine for the treatment of Flaviviridae infections. Idenix has reported clinical trials for a related compound NM283 which is believed to be the valine ester 5 of the cytidine analog 2 (B=cytosine). In WO 2004/002999 published Jan. 8, 2004, J.-P. Sommadossi et al. disclose a series of 2' or 3'prodrugs of 1', 2', 3', or 4' branched nucleosides for the treatment of flavivirus infections including HCV infections.

In WO2004/046331 published Jun. 3, 2004, J.-P. Sommadossi et al. disclose 2'-branched nucleosides and Flaviviridae mutation. In WO03/026589 published Apr. 3, 2003 G. Gosselin et al. disclose methods of treating hepatitis C virus using 4'-modified nucleosides. In WO2005009418 published Feb. 3, 2005, R. Storer et al. disclose purine nucleoside analogues for treatment of diseases caused by Flaviviridae including HCV.

Other patent applications disclose the use of certain nucleoside analogs to treat hepatitis C virus infection. In WO 01/32153 published May 10, 2001, R. Storer discloses nucleosides derivatives for treating viral diseases. In WO 01/60315 published Aug. 23, 2001, H. Ismaili et al., disclose methods of treatment or prevention of Flavivirus infections with nucleoside compounds. In WO 02/18404 published Mar. 7, 2002, R. Devos et al. disclose 4'-substituted nucleotides for treating HCV virus. In WO 01/79246 published Oct. 25, 2001, K. A. Watanabe disclose 2'- or 3'-hydroxymethyl nucleoside compounds for the treatment of viral diseases. In WO 02/32920 published Apr. 25, 2002 and in WO 02/48 165 published Jun. 20, 2002 L. Stuyver et al. disclose nucleoside compounds for the treatment of viral diseases.

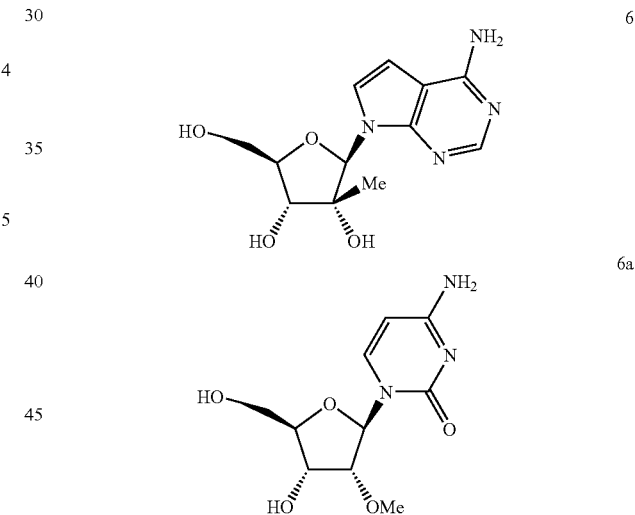

In WO 03/105770 published Dec. 24, 2003, B. Bhat et al. disclose a series of carbocyclic nucleoside derivatives that are useful for the treatment of HCV infections. In WO 2004/007512 published Jan. 22, 2003 B. Bhat et al. disclose nucleoside compounds that inhibit of RNA-dependent RNA viral polymerase. The nucleosides disclosed in this publication are primarily 2'-methyl-2'-hydroxy substituted nucleosides. In WO 2002/057425 published Jul. 25, 2002 S. S. Carroll et al. disclose nucleoside derivatives which inhibitor of RNA-dependent viral polymerase and methods of treating HCV infection. In WO02/057287 published Jul. 25, 2002, S. S. Carroll et al. disclose related 2α-methyl and 2β-methylribose derivatives wherein the base is an optionally substituted 7H-pyrrolo [2,3-d]pyrimidine radical 6. The same application discloses one example of a 3β-methyl nucleoside. S. S. Carroll et al. (*J. Biol. Chem.* 2003 278(14):11979-11984) disclose inhibition of HCV polymerase by 2'-O-methylcytidine (6a). In WO 2004/009020 published Jan. 29, 2004, D. B. Olsen et al. disclose a series of thionucleoside derivatives as inhibitors of RNA dependent RNA viral polymerase.

PCT Publication No. WO 99/43691 to Emory University, entitled "2'-Fluoronucleosides" discloses the use of certain 2'-fluoronucleosides to treat HCV. U.S. Pat. No. 6,348,587 to Emory University entitled "2'-fluoronucleosides" discloses a family of 2'-fluoronucleosides useful for the treatment of hepatitis B, HCV, HIV and abnormal cellular proliferation. Both configurations of the 2' fluoro substituent are disclosed.

Eldrup et al. (Oral Session V, Hepatitis C Virus, Flaviviridae; 16$^{th}$ International Conference on Antiviral Research (Apr. 27, 2003, Savannah, Ga.)) described the structure activity relationship of 2'-modified nucleosides for inhibition of HCV.

Bhat et al. (Oral Session V, Hepatitis C Virus, Flaviviridae; 16$^{th}$ International Conference on Antiviral Research (Apr. 27, 2003, Savannah, Ga.); p A75) describe the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; 16$^{th}$ International Conference on Antiviral Research (Apr. 27, 2003, Savannah, Ga.) p A76) also described the effects of the 2'-modified nucleosides on HCV RNA replication.

Non-nucleoside allosteric inhibitors of HIV reverse transcriptase have proven effective therapeutics alone and in combination with nucleoside inhibitors and with protease inhibitors. Several classes of non-nucleoside HCV NS5B inhibitors have been described and are currently at various stages of development including: benzimidazoles, (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1); indoles, (P. L. Beaulieu et al. WO 03/0010141 A2); benzothiadiazines, e.g., 7, (D. Dhanak et al. WO 01/85172 A1; D. Dhanak et al. WO 03/037262 A2; K. J. Duffy et al. WO03/099801 A1, D. Chai et al. WO 2004052312, D. Chai et al. WO2004052313, D. Chai et al. WO02/098424, J. K. Pratt et al. WO 2004/041818 A1; J. K. Pratt et al. WO 2004/087577 A1), thiophenes, e.g., 8, (C. K. Chan et al. WO 02/100851);

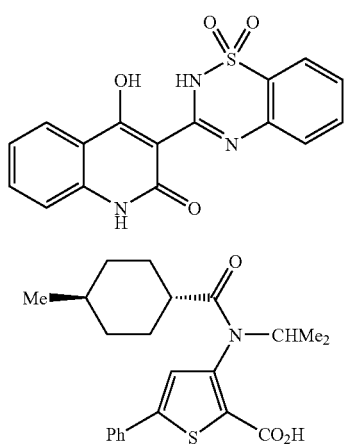

benzothiophenes (D. C. Young and T. R. Bailey WO 00/18231); β-ketopyruvates (S. Attamura et al. U.S. Pat. No. 6,492,423 B1, A. Attamura et al. WO 00/06529); pyrimidines (C. Gardelli et al. WO 02/06246 A1); pyrimidinediones (T. R. Bailey and D. C. Young WO 00/13708); triazines (K.-H. Chung et al. WO 02/079187 A1); rhodanine derivatives (T. R. Bailey and D. C. Young WO 00/10573, J. C. Jean et al. WO 01/77091 A2); 2,4-dioxopyrans (R. A. Love et al. EP 256628 A2); phenylalanine derivatives (M. Wang et al. *J. Biol. Chem.* 2003 278:2489-2495).

The NS3 protease has emerged as a major target for discovery of new anti-HCV therapy. In WO 98/22496 published May 28, 1998, M. R. Attwood et al. have disclosed mechanism-base active site inhibitors of the protease (M. R. Attwood et al, *Antiviral Chemistry and Chemotherapy* 1999 10:259-273; M. R. Attwood et al., Preparation and use of amino acid derivatives as anti-viral agents, German Patent Pub. DE 19914474). In WO98/17679 published Apr. 30, 1998 R. D. Tung et al. disclosed mechanism-based peptide inhibitors on the NS3 protease.

In WO99/07734 published Feb. 18, 1999 and in WO00/09543 published Aug. 9, 1999, M Llinas-Brunet et al. disclose peptide inhibitors of the protease. In WO00/59929 published Oct. 12, 2000, Y. S. Tsantrizos et al. disclose macrocyclic tripeptides which are potent inhibitors of the HCV NS3 protease. A series of related patents from Boehringer-Ingleheim disclose related protease inhibitors and have lead to the identification of tripeptide derivative BILN 2061 (M. Llinas-Brunet et al. *Biorg. Med. Chem. Lett.* 2000 10(20):2267-70; *J. Med Chem.* 2004 47(26):6584-94; *J. Med. Chem.* 2004 47(7):1605-1608; *Angew. Chem. Int. Ed. Eng.* 2003 42(12):1356-60).

Other tripeptide inhibitors identified by Bristol-Myers Squibb have been disclosed, inter alia, in WO03/099274 published Dec. 4, 2003, in WO2004/032827 published Apr. 22, 2004, in WO03/053349 published Jul. 3, 2003, in WO2005/046712 published May 26, 2005 and in WO2005/051410 published Jun. 9, 2005. In WO2004/072234 published Aug. 26, 2004 and in WO2004/093798 published Nov. 4, 2004 further tripeptide protease inhibitors were disclosed by Enanta Pharmaceuticals. In WO2005/037214 published Apr. 28, 2005 L. M. Blatt et al. disclose still other tripeptide derivatives that inhibit HCV NS3 protease. In WO2005/030796 published Apr. 7, 2005, S. Venkatraman et al. disclose macrocyclic inhibitors of HCV NS3 serine protease. In WO 2005/058821 published Jun. 30, 2005, F. Velazquez et al. disclose inhibitors of HCV NS3/NS4a serine protease. In WO02/48172 published Jun. 20, 2002, Z. Zhu disclose diaryl peptides as inhibitors of NS3 protease. In WO02/08187 and in WO02/08256 both published Jan. 31, 2002, A. Saksena et al. disclose peptide inhibitors of HCV NS3 protease. In WO02/08251 published Jan. 31, 2002 M. Lim-Wilby et al. disclose peptide inhibitors of the NS3 protease. In U.S. Pat. No. 6,004,933 published Dec. 21, 1999, L. W. Spruce et al. disclose heterocyclic peptide derivatives which inhibit cysteine proteases including HCV endopeptidase.

Non-substrate-based NS3 protease inhibitors such as 2,4,6-trihydroxy-3-nitro-benzamide derivatives (Sudo K. et al., *BBRC* 1997 238:643-647; Sudo K. et al. *Antiviral Chemistry and Chemotherapy* 1998 9:186), including RD3-4082 and RD3-4078, the former substituted on the amide with a 14 carbon chain and the latter processing a para-phenoxyphenyl group are also being investigated.

SCH 68631, a phenanthrenequinone, is an HCV protease inhibitor (Chu M. et al. *Tetrahedron Lett.* 1996 37:7229-7232). In another example by the same authors, SCH 351633, isolated from the fungus *Penicillium griseofulvum*, was identified as a protease inhibitor (Chu M. et al., *Bioorg. Med. Chem. Lett.* 1999 9:1949-1952). Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin (Qasim M. A. et al., *Biochemistry* 1997 36:1598-1607).

Thiazolidine derivatives which show relevant inhibition in a reverse-phase HPLC assay with an NS3/4A fusion protein and NS5A/5B substrate (Sudo K. et al. *Antiviral Research* 1996 32:9-18), especially compound RD-1-6250, possessing a fused cinnamoyl moiety substituted with a long alkyl chain, RD4 6205 and RD4 6193. Thiazolidines and benzanilides were identified by N. Kakiuchi et al. in *FEBS Let.* 1998 421:217-220 and N. Takeshita et al. *Anal. Biochem.* 1997 247:242-246.

Imidazolidinones as NS3 serine protease inhibitors of HCV are disclosed in WO 02/08198 to Schering Corporation published Jan. 31, 2002 and in WO 02/48157 to Bristol Myers Squibb published Jun. 20, 2002. In WO02/48116 published Jun. 20, 2002 P. Glunz et al. disclose pyrimidinone inhibitors of NS3 protease.

Other enzymatic targets for anti-HCV include the HCV IRES site (Internal Ribosomal Entry Site) and HCV helicase. IRES inhibitors have been reported by Immusol, Rigel Pharmaceuticals (R803) and by Anadys (ANA 245 and ANA 246). Vertex has disclosed an HCV helicase inhibitor.

Combination therapy which can suppress resistant mutant strains, has become well established approach to anti-viral chemotherapy. The nucleoside inhibitors disclosed herein can be combined with other nucleoside HCV polymerase inhibitors, non-nucleoside HCV polymerase inhibitors, and HCV protease inhibitors. As other classes of HCV drugs, e.g. viral entry inhibitors, helicase inhibitors, IRES inhibitors, ribozymes and antisense oligonucleotides emerge and are developed they will also be excellent candidates for combination therapy. Interferon derivatives have already been successfully combined with ribavirin and interferons and chemically modified interferons will be useful in combination with the nucleosides herein disclosed.

Nucleoside Prodrugs

Nucleoside derivatives often are potent anti-viral (e.g., HIV, HCV, Herpes simplex, CMV) and anti-cancer chemotherapeutic agents. Unfortunately their practical utility is often limited by two factors. Firstly, poor pharmacokinetic properties frequently limit the absorption of the nucleoside from the gut and the intracellular concentration of the nucleoside derivatives and, secondly, suboptimal physical properties restrict formulation options which could be employed to enhance delivery of the active ingredient.

Albert introduced the term prodrug to describe a compound which lacks intrinsic biological activity but which is capable of metabolic transformation to the active drug substance (A. Albert, *Selective Toxicity*, Chapman and Hall, London, 1951). Produgs have been recently reviewed (P. Ettmayer et al., *J. Med Chem.* 2004 47(10):2393-2404; K. Beaumont et al., *Curr. Drug Metab.* 2003 4:461-485; H. Bundgaard, *Design of Prodrugs: Bioreversible derivatives for various functional groups and chemical entities in Design of Prodrugs*, H. Bundgaard (ed) Elsevier Science Publishers, Amersterdam 1985; G. M. Pauletti et al. *Adv. Drug Deliv. Rev.* 1997 27:235-256; R. J. Jones and N. Bischofberger, *Antiviral Res.* 1995 27; 1-15 and C. R. Wagner et al., *Med. Res. Rev.* 2000 20:417-45). While the metabolic transformation can catalyzed by specific enzymes, often hydrolases, the active compound can also be regenerated by non-specific chemical processes.

Pharmaceutically acceptable prodrugs refer to a compound that is metabolized, for example hydrolyzed or oxidized, in the host to form the compound of the present invention. The bioconversion should avoid formation fragments with toxicological liabilities. Typical examples of prodrugs include compounds that have biologically labile protecting groups linked to a functional moiety of the active compound. Alkylation, acylation or other lipophilic modification of the hydroxy group(s) on the sugar moiety have been utilized in the design of pronucleotides. These pronucleotides can be hydrolyzed or dealkylated in vivo to generate the active compound. Factors limiting oral bioavailability frequently are absorption from the gastrointestinal tract and first-pass excretion by the gut wall and the liver. Optimization of transcellular absorption through the GI tract requires a $D_{(7,4)}$ greater than zero. Optimization of the distribution coefficient does not, however, insure success. The prodrug may have to avoid active efflux transporters in the enterocyte. Intracellular metabolism in the enterocyte can result in passive transport or active transport of the metabolite by efflux pumps back into the gut lumen. The prodrug must also resist undesired biotransformations in the blood before reaching the target cells or receptors.

While putative prodrugs sometimes can rationally designed based on the chemical functionality present in the molecule, chemical modification of an active compound produces an entirely new molecular entity which can exhibit undesirable physical, chemical and biological properties absent in the parent compound. Regulatory requirements for identification of metabolites may pose challenges if multiple pathways lead to a plurality of metabolites. Thus, the identification of prodrugs remains an uncertain and challenging exercise. Moreover, evaluating pharmacokinetic properties of potential prodrugs is a challenging and costly endeavor. Pharmacokinetic results from animal models may be difficult to extrapolate to humans.

The object of the present invention is to provide new compounds, methods and compositions for the treatment of a host infected with hepatitis C virus.

SUMMARY OF THE INVENTION

The present invention is directed toward novel di-acyl derivatives of 4-amino-1-((2R,3R,4R,5R)-3-fluoro-4-hydroxy-5-hydroxymethyl-3-methyl-tetrahydro-furan-2-yl)-1H-pyrimidin-2-one (also referred to as (2R)2'-deoxy-2-methyl-2-fluoro-cytidine). Compounds of the present invention possesses a structure according to formula I.

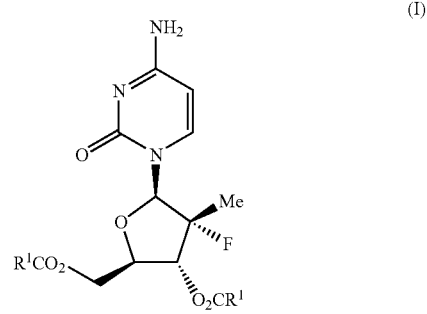

(I)

wherein:

R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy; and, hydrates, solvates and acid addition salts thereof.

Compounds of the present invention are useful for treating a disorder mediated by HCV the invention further comprises methods of treating HCV with compounds of the present invention and pharmaceutical compositions containing said compounds.

DETAILED DESCRIPTION OF THE INVENTION

In one embodiment of the present invention there is provided a compound according to formula I wherein R$^1$ is as defined herein above.

In another embodiment of the present invention there is provided a compound according to formula I wherein R$^1$ is ethyl, n-propyl, iso-propyl, n-butyl or iso-butyl.

In still another embodiment of the present invention there is provided a compound according to formula I wherein R$^1$ is ethyl or iso-propyl.

In yet another embodiment of the present invention there is provided a compound according to formula I wherein R$^1$ is iso-propyl and the compound is a hydrochloride or sulfate salt.

In still another embodiment of the present invention there is provided a compound according to formula I wherein R$^1$ is ethoxy, n-propoxy or iso-propoxy.

In still another embodiment of the present invention there is provided a method for treating a disease mediated by the HCV comprising administering to a patient in need thereof a therapeutically effective dose of a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy, or a hydrates, solvates or acid addition salts thereof.

In still another embodiment of the present invention there is provided a method for treating a disease mediated by the HCV comprising administering to a patient in need thereof dose of 0.1 to 10 g per day of a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy or a hydrates, solvates or acid addition salts thereof. In yet another embodiment the dose is between 0.5 and 7 g per day and in a further embodiment the dose is between 1.0 and 6.0 g per day.

In another embodiment of the present invention there is provided a method for treating a disease mediated by the HCV comprising co-administering to a patient in need thereof a therapeutically effective dose of a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy or a hydrates, solvates or acid addition salts thereof and a therapeutically effective amount of at least one immune system modulator and/or at least one antiviral agent that inhibits replication of HCV.

In another embodiment of the present invention there is provided a method for treating a disease mediated by the HCV comprising co-administering to a patient in need thereof a therapeutically effective dose of a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy or a hydrates, solvates or acid addition salts thereof and a therapeutically effective amount of at least one immune system modulator which immune system modulator is an interferon, interleukin, tumor necrosis factor or colony stimulating factor.

In another embodiment of the present invention there is provided a method for treating a disease mediated by the HCV comprising co-administering to a patient in need thereof a therapeutically effective dose of a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy or a hydrates, solvates or acid addition salts thereof, and a therapeutically effective amount of at least one immune system modulator which immune system modulator is an interferon or a chemically derivatized interferon.

In another embodiment of the present invention there is provided a method for treating a disease mediated by the HCV comprising co-administering to a patient in need thereof a therapeutically effective dose of a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy or a hydrates, solvates or acid addition salts thereof, and a therapeutically effective amount of at least one other antiviral compound.

In another embodiment of the present invention there is provided a method for treating a disease mediated by the HCV comprising co-administering to a patient in need thereof a therapeutically effective dose of a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy or hydrates, solvates or acid addition salts thereof, and a therapeutically effective amount of at least one other antiviral compound which compound is a HCV protease inhibitor, another nucleoside HCV polymerase inhibitor, a non-nucleoside HCV polymerase inhibitor, an HCV helicase inhibitor, an HCV primase inhibitor or a HCV fusion inhibitor.

In another embodiment of the present invention there is provided a pharmaceutical composition of comprising a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy or a hydrates, solvates or acid addition salts thereof admixed with at least one pharmaceutically acceptable carrier, diluent or excipient.

In another embodiment of the present invention there is provided a process for the preparation of a compound according to formula I wherein R$^1$ is selected from the group consisting of C$_{2-5}$ unbranched or branched alkyl, C$_{2-5}$ unbranched or branched alkenyl, C$_{2-5}$ unbranched or branched alkynyl, C$_{2-5}$ lower haloalkyl, C$_{3-6}$ cycloalkyl, and C$_{2-4}$ alkoxy which process comprises steps (i)-(v) enumerated claim 15 and exemplified in the examples. The process comprises treating I in a basic aqueous organic media which can be homogenous or biphasic with an acylating agent as defined herein in the presence of DMAP and sufficient base to maintain the solution at a pH of at least about 7.5. The present process allows the acylation without concomitant reaction of the heterocyclic base.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the first definition provided in the Summary of the Invention.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "independently" is used herein to indicate that a variable is applied in any one instance without regard to the presence or absence of a variable having that same or a different definition within the same compound. Thus, in a compound in which R appears twice and is defined as "independently carbon or nitrogen", both R's can be carbon, both R's can be nitrogen, or one $R^1$ can be carbon and the other nitrogen.

The term "alkenyl" as used herein denotes an unsubstituted hydrocarbon chain radical having from 2 to 10 carbon atoms having one or two olefinic double bonds [preferably one olefinic double bond]. $C_{2-10}$ alkenyl" as used herein refers to an alkenyl composed of 2 to 10 carbons. Examples are vinyl, 1-propenyl, 2-propenyl (allyl) or 2-butenyl (crotyl).

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

The term "alkynyl" as used herein denotes an unbranched or branched hydrocarbon chain radical having from 2 to 10 carbon atoms, preferably 2 to 5 carbon atoms, and having one triple bonds. $C_{2-10}$ alkynyl" as used herein refers to an alkynyl composed of 2 to 10 carbons Examples are ethynyl, 1-propynyl, 2-propynyl, 1-butynyl, 2-butynyl or 3-butynyl.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "haloalkyl" as used herein denotes a unbranched or branched chain alkyl group as defined above wherein 1, 2, 3 or more hydrogen atoms are substituted by a halogen. "$C_{1-3}$ haloalkyl" as used herein refers to an haloalkyl composed of 1 to 3 carbons and 1-8 halogen substituents. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkoxy" as used herein means an —O-alkyl group, wherein alkyl is as defined above. Examples are methoxy, ethoxy, n-propyloxy, i-propyloxy, n-butyloxy, i-butyloxy, t-butyloxy. "Lower alkoxy" as used herein denotes an alkoxy group with a "lower alkyl" group as previously defined. "$C_{1-10}$ alkoxy" refers to an —O-alkyl wherein alkyl is $C_{1-10}$.

The term "di-acyl" derivative as used herein refers to a derivatized nucleoside compound as described herein wherein the 3'- and 5'-hydroxy are from an ester —OC(═O)$R^1$ and OC(═O)$R^2$ where $R^1$ and $R^2$ are as defined in claim 1.

The term "acylating agent" as used herein refers to either an anhydride, acid halide, chlorocarbonylalkoxide (e.g. ethyl chloroformate) or an activated derivative of an N-protected alpha amino acid. The term "anhydride" as used herein refers to compounds of the general structure $R^1$C(O)—O—C(O)$R^1$ wherein $R^1$ is as defined in claim 1. The term "acid halide" as used herein refers to compounds of the general structure $R^1$C(O)X wherein X is a halogen. The term "acyl imidazole" refers to a compound of general structure $R^1$C(O)X wherein X is N-imidazolyl. The term "activated derivative" of a compound as used herein refers to a transient reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance and corresponding activating agents or groupings which activate the carboxy group are described in more detail below. Of particular interest for the present invention is carboxylic acid anhydrides and carboxylic acid chlorides.

The phrase "heterogeneous aqueous solvent mixture" as used here refers to a mixture of water and an organic co-solvent which produces a two-phase or heterogeneous mixture. This heterogeneous aqueous solvent mixture may result from a co-solvent with limited aqueous solubility or the ionic strength of the aqueous component can be adjusted to limit the solubility of the co-solvent in the aqueous phase.

The term "alkali metal hydroxide" refers to a compound of formula MOH wherein M is lithium sodium, potassium or cesium, "alkali metal bicarbonate" refers to a group $MHCO_3$ wherein M is sodium or potassium and "alkali metal carbonate" refers to a group $M_2CO_3$ where M is sodium or potassium. One skilled in the art will appreciate that other bases can be used to maintain the pH with desired range and other bases are within the scope of the invention.

Abbreviations used in this application include: acetyl (Ac), acetic acid (HOAc), 1-N-hydroxybenzotriazole (HOBt), atmospheres (Atm), high pressure liquid chromatography (HPLC), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms), methyl t-butyl ether (MTBE), 1,5-diazabicyclo[4.3.0]non-5-ene (DBN), 1,8-diazabicyclo[5.4.0]undec-7-ene (DBU), N-methylmorpholine (NMM), N-methylpyrrolidone (NMP), 1,2-dichloroethane (DCE), N,N'-dicyclohexylcarbodiimide (DCC), pyridinium dichromate (PDC), dichloromethane (DCM), propyl (Pr), pounds per square inch (psi), diisopropylethylamine (DIPEA, Hunig's Base), pyridine (pyr), room temperature, rt or RT, N,N-dimethyl acetamide (DMA), tert-butyldimethylsilyl or t-$BuMe_2Si$, (TBDMS), 4-N,N-dimethylaminopyridine (DMAP), triethylamine ($Et_3N$ or TEA), N,N-dimethylformamide (DMF), dimethyl sulfoxide (DMSO), trifluoroacetic acid (TFA), thin layer chromatography (TLC), ethyl acetate (EtOAc), tetrahydrofuran (THF), diethyl ether (Et$_2$O), trimethylsilyl or Me$_3$Si (TMS), ethyl (Et), p-toluenesulfonic acid monohydrate (TsOH or pTsOH), 4-Me-C$_6$H$_4$SO$_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Examples of representative compounds encompassed by the present invention and within the scope of the invention are provided in TABLE I. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, by bold or dashed lines, the structure or portion of the structure is to be interpreted as encompassing all stereoisomers of it. The numbering system for these ring systems is as follows:

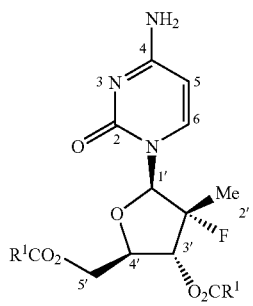

Compounds and Preparation

The HCV polymerase inhibitory activity of (2R)-2'-deoxy-2'-fluoro-2'-C-methylcytidine has been disclosed (J. L. Clark et al. *J. Med. Chem.* 2005 48(17):5504-8; J. Clark U.S. Publication No. 2005/0009737 and both publications are hereby incorporated by reference in their entirety). In clinical practice, it would be desirable to initially administer high doses of I-6 to quickly inhibit HCV polymerase and thereby lower viral levels under conditions that minimize the opportunity for the virus to mutate and to select for resistant strains. Sufficiently high levels may by difficult to achieve with the parent nucleoside. Prodrugs provide one strategy to improve the pharmacokinetic and physical properties of a compound and thereby optimize the bioavailability. The U.S. Publication 2005/0009737 suggests general approaches to nucleoside prodrugs of 2'-deoxy-2'-fluoro-2'-methyl nucleosides. While prodrug candidates are deceptively simple to envision, the identification of compounds with the appropriate physiochemical and pharmacodynamic properties, in vivo transformations and safety profile is a complex multi-disciplinary undertaking that requires significant experimentation. Hurdles to identification of prodrugs for oral delivery include maintaining sufficient aqueous solubility, lipophilicity and chemical stability at the same time as enabling rapid and efficient release of the active moiety post administration. Additionally significant non-esterase metabolism and transporter mediated clearance of the prodrug must be minimized (K. Beaumont et al. *Curr. Drug Metab.* 2003 4(6):461-485). Also inhibition or induction of cytochrome P$_{450}$ enzymes can produce untoward drug-drug interactions which are undesirable. Lower alkyl diesters of I-6 depicted in TABLE 1 have surprisingly been found to significantly improve the bioavailability of I-6.

The pharmacokinetic behavior of potential prodrugs was assessed in both the rat and monkey to attempt to minimize intra-species variability and genetic polymorphisms which may result in intra-species artifacts. To the extent that enzymatic transformations are responsible for hydrolysis of the ester linkages the specific affinity for the prodrug may depend on the specific structure of the esterase and/or peptidase which could catalyze the transformation. Rat esterase activity has frequently been shown to be significantly higher than man (J. A. Fix et al. *Pharm. Res.* 1990 7(4):384-387; W. Li et al. *Antimicrob. Agents Chemother* 1998 42(3):647-653). Another potentially important parameter was the bioconversion of the cytidine base to uridine by a deaminase. Although the triphosphates of cytidine and uridine are polymerase inhibitors, in vivo phosphorylation of uridine is inefficient compared to cytidine. Thus increased uridine levels are considered undesirable. The lack of efficacy exhibited by the uridine derivative in the HCV replicon (J. Clark et al. *J. Med. Chem.*, supra) has been reported.

TABLE 1

| Cpd. No. | R | mp | Caco-2 (2-7d) $P_{app}$ (×10$^{-6}$ cm/sec) | Rat $C_{max}$[1] AUC(cyt)[2] AUC(urd) | Monkey $C_{max}$ AUC(cyt) AUC(urd) |
|---|---|---|---|---|---|
| I-1 | C(=O)-n-C$_4$H$_9$ | 157-158.8 | 23.2 | 0.65<br>9.8(parent)<br>7.7(uridine) | 0.9<br>8.3<br>0.3 |

TABLE 1-continued

Structure: cytidine analog with RO- at 5', RO at 3', F and Me at 2' position, cytosine base (NH$_2$, N, O).

| Cpd. No. | R | mp | Caco-2 (2-7d) $P_{app}$ (×10$^{-6}$ cm/sec) | Rat $C_{max}$[1] AUC(cyt)[2] AUC(urd) | Monkey $C_{max}$ AUC(cyt) AUC(urd) |
|---|---|---|---|---|---|
| I-2 | C(=O)-i-C$_3$H$_7$ | 190.4-190.9 | 3.93, 4.62, 6.04 | —<br>25.7<br>7.8 | 1.88<br>16.17<br>0.13 |
| I-3 | C(=O)—C$_2$H$_5$ | 185.2-186.0 | 3.01, 1.06, 1.02 | —<br>22.4<br>5.38 | 1.2<br>9.3<br>0.16 |
| I-4 | C(=O)—O—CH$_2$CHMe$_2$ | 210.0-211.5 | 6.4 | 1.2<br>13.6<br>3.8 | 1.1<br>9.2<br>0.2 |
| I-5 | C(=O)—O-n-C$_3$H$_7$ | 192.0-194.4 | 13.4 | | 0.97<br>6.2<br>0.19 |
| I-6 | H[3] | | 0.4 | 0.82<br>5.6<br>5.4 | 0.6<br>2.97<br>0.9 |

[1] Cmax is the peak concentration of the I-7 in the blood.
[2] AUC(cyt) is the area-under-the curve for cytidine nucleoside AUC(urd) is the area-under-the curve for uridine nucleoside
[3] EC$_{90}$ in replicon is 5.40 ± 2.6 μM (J. Clark et al. J. Med. Chem., supra)

Surprisingly, it has now been found that C$_{2-5}$ alkyl diesters of I-6 exhibit excellent prodrug properties. Substantially higher levels of the fluorinated nucleoside are observed in the blood in both rat and monkey. Furthermore the ratio of cytidine to uridine in the fluorinated base is higher in both species when the nucleoside was administered as the diester.

Furthermore, diesters are capable of forming two different monoesters and the non-esterified nucleoside. The pharmacokinetic analysis in this situation can be complex if all the species are present in blood in significant concentrations. The presence of multiple metabolites in the blood adds additional burdens to establish that the prodrug is safe. Surprisingly hydrolysis of the both esters is quite facile and the only significant metabolite observed in the blood in addition to the parent nucleoside is the 3'-monoester which rapidly is converted to I-6.

To further evaluate potential behavior in human subjects, the transport through Caco-2 cells was evaluated for the putative prodrugs. Caco-2 cells are commonly used to evaluated the potential absorption/permeability of molecules (G. Gaviraghi et al. in *Pharmacokinetic optimization in drug research. Biological, Pharmacokinetic and Computational Strategies*. B. Testa et al. eds. Wiley Interscience VCH, Zurich 2001 pp 3-14). Caco-2 permeability was found to be acceptable for C$_{2-5}$ alkyl diesters of I-6.

In addition to efficient in vivo biotransformation a prodrug for oral administration also must exhibit suitable physiochemical properties to formulate the drug and insure absorption from the gut into a compartment where the desired biotransformation can occur. Particularly relevant are water solubility, partition coefficient and stability in gastric and intestinal fluids. Values for these parameters are displayed in TABLE 2.

TABLE 2

| | $K_{O/W}$[1] | log D[2] | Solubility.[3] | SGF[4] $T_{1/2}$(h) 37° C. | SIF[5] $T_{1/2}$(h) 37° C. |
|---|---|---|---|---|---|
| I-1 | 3.39 | ND[7] | 0.016 | 18.6 | >8.4[11] |
| I-2 | 2.33 | 1.67 | 0.18[6] | 25.1 | 866 |
| I-3 | 1.27 | 0.9 | 3.7[8] | 9 | 72 |
| I-4 | 3.00 | ND | 0.013[9] | >7[11] | >15[11] |
| I-5 | 2.20 | ND | 0.13 | >10.4[11] | >11[11] |
| I-6 | −0.94 | ND | 76 | >12[11] | >12[11] |

[1] Calculated octanol/water partition coefficient
[2] Experimentally determined distribution coefficient at pH 7.4
[3] Solubility in aqueous media, water, or buffer pH 6.5 (mg/mL).
[4] Stability in simulated gastric fluid (SGF; pH 1.2)
[5] Stability in simulated intestinal fluid (SIF; pH 7.4)
[6] Solubility in SGF is 13.3 mg/mL
[7] not determined
[8] Media is SIF, solubility in SGF is 13.6 mg/mL
[9] Media is SIF, solubility in SGF is 0.16 mg/mL
[10] Measured in water and pH 6 buffer
[11] Insignificant degradation noted over the time period
[12] Determined at pH 5.5

The oil-water partition coefficient $P_{O/W}$ (clogP is the calculated $P_{O/W}$) is an important property for orally administered drugs. The drug substance must have sufficient aqueous solubility to dissolve in the formulation and the gastrointestinal (GI) fluids to contact the endothelial cells in the stomach and intestine and sufficient lipid solubility to traverse through the lipid bilayer membrane of these cells and ultimately into the blood. The optimal range for the log P of a compound for oral bioavailability is between 1 and 3 which is exhibited by compounds of the present invention.

The expression $P_{O/W}$ as used herein refers to the octanol/water partition coefficient. The expression clogP as used herein refers to the calculated $P_{O/W}$. Computer programs which calculate $P_{O/W}$ are readily available to the pharmaceutical and medicinal chemist. The term distribution coefficient refers to the experimentally determined partition coefficient between octanol and a buffered aqueous solution. The partition coefficient and distribution coefficient are generally similar but the latter is a function of the pH of the aqueous solution whereas the $P_{O/W}$ is independent of pH.

The solubility in water of a orally administered prodrug should be greater than at least about 0.1 mg/mL for optimal formulation and the half-lives in simulated gastric fluid and simulated intestinal fluid should be 1-2 h and 2-4 h respectively to allow sufficient time to traverse the stomach and be absorbed in the intestine.

The compounds of the present invention are conveniently prepared in one step by acylation of I-6 in an aqueous organic solvent. The solvent can either be a homogenous aqueous solution or a two-phase solution. The pH of the aqueous organic solvent is maintained above 7.5 by addition of base to neutralize acid produced by the acylation. The base can be either an alkali or alkaline metal hydroxide or a tertiary amine. The reaction is carried out in the presence of DMAP which is known in the art to be a catalyst for acylation. An advantage of the present process is the desired product can be obtained without acylation of the heterocyclic base. No protecting group is required which eliminates the need for a protection/deprotection step. The process is described in the accompanying examples.

Dosage and Administration

The compounds of the present invention may be formulated in a wide variety of oral administration dosage forms and carriers. Oral administration can be in the form of tablets, coated tablets, hard and soft gelatine capsules, solutions, emulsions, syrups, or suspensions. Compounds of the present invention are efficacious when administered by suppository administration, among other routes of administration. The most convenient manner of administration is generally oral using a convenient daily dosing regimen which can be adjusted according to the severity of the disease and the patient's response to the antiviral medication.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound as used herein means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (e.g., salt formulation), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.1 and about 10 g per day should be appropriate in monotherapy and/or in combination therapy. A preferred daily dosage is between about 0.5 and about 7.5 g per day, more preferred 1.5 and about 6.0 g per day. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on personal knowledge, experience and the disclosures of this application, to ascertain a therapeutically effective amount of the compounds of the present invention for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

In embodiments of the invention, the active compound or a salt can be administered in combination with another antiviral agent such as ribavirin, another nucleoside HCV polymerase inhibitor, a HCV non-nucleoside polymerase inhibitor, a HCV protease inhibitor, a HCV helicase inhibitor or a HCV fusion inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

Example 1

Propionic acid (2R,3R,4R,5R)-5-(4-amino-2-oxo-2H-pyrimidin-1-yl)-4-fluoro-4-methyl-3-propionyloxy-tetrahydro-furan-2-ylmethyl ester (I-3)

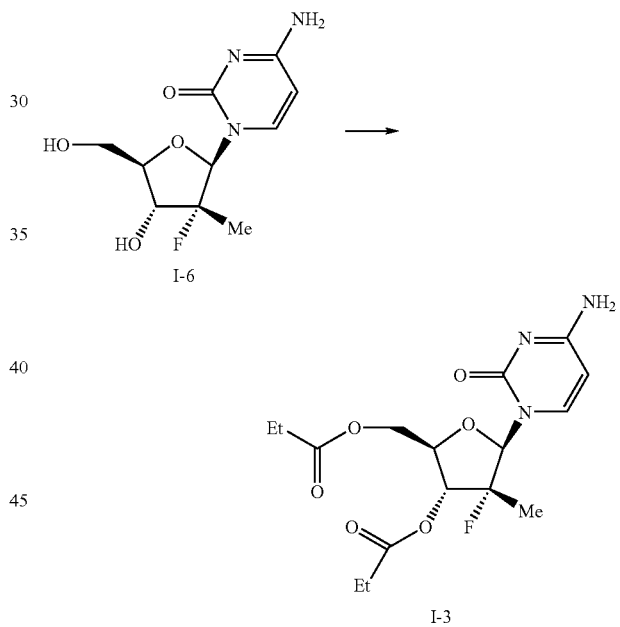

To a suspension of I-6 (30 g, 0.116 mol), DMAP (1.4 g, 11.57 mmol) in THF (300 mL) and water (150 mL) was added TEA (35.1 g, 0.347 mol) to obtain a clear solution (pH about 11). The reaction mixture was cooled to 5-10° C. and propionic anhydride (30.1 g, 0.231 mol) was added dropwise to the stirred biphasic reaction. The pH was monitored and maintained at about 11-12 by simultaneous addition of KOH solution. The progress of the reaction was monitored by HPLC analysis and after the propionyl chloride was added there was about 52% of the diester, 30% monoesters and 15% starting material. Additional propionic anhydride (45.2 g, 0.347 mol) was added dropwise under the conditions described above. The reaction mixture was allowed to stand overnight without stirring. The HPLC of the organic phase indicated ca. 96% diester and ca 2% monoester. The phases were separated and the aqueous phase twice extracted with THF (100 mL). The combined organic phases were washed with brine. The organic phase is filtered, evaporated and the residue dissolved in water (ca. 500 mL) and then diluted with IPA (ca. 100 mL). The resulting mixture is slowly cooled to ambient temperature with stirring. The resulting precipitate was filtered, washed with water and heptane, dried at about 60° C. under vacuum for ca. 60 h to afford 3.45 g (80.3%) of I-3 which was 98.75% pure by HPLC.

Example 2

Isobutyric acid (2R,3R,4R,5R)-5-(4-amino-2-oxo-2H-pyrimidin-1-yl)-4-fluoro-3-isobutyryloxy-4-methyl-tetrahydro-furan-2-ylmethyl ester (I-2)

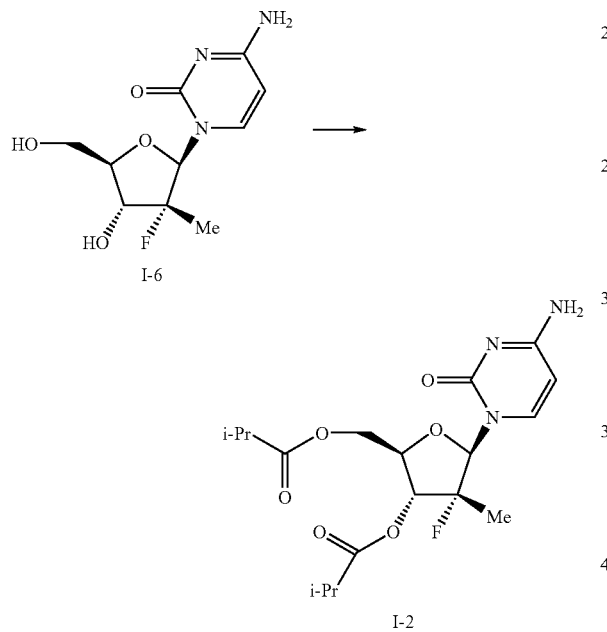

To an ice-cold suspension of I-6 (970 g, 3.74 mol) and DMAP (50 g, 0.412 mol) in THF (10 L). was added TEA (2.3 kg, 16.5 mol) and water (7 L) which produced a clear solution. Isobutyryl chloride (3 equivalents) was added slowly to the stirred mixture while maintaining the temperature at ca. 0° C. An additional 1.2 then 0.7 equivalents of isobutytyl chloride was added until the HPLC indicated the reaction had proceeded essentially to completion (a total of ca. 1.95 kg). The reaction mixture was acidified with con HCl to a pH of ca 6.4 and the organic phase was washed with EtOAc (2×10 L). The combined extracts were washed with water (1×15 L). The organic phase is filtered and concentrated in vacuo. The residue was dissolved in IPA (ca. 20 kg) and heptane (14.2 kg) was added. The solution was heated to ca. 74-75° C. to produce a clear solution, then ca 5 L was removed by distillation. The resulting solution was cooled slowly to RT. A precipitate formed at ca. 42-43° C. Cooling was continued slowly to 5° C. then stirred overnight. The resulting solid was filtered and the filtrate was washed with IPA/heptane (1:8) mixture (13.4 kg), dried under vacuum at about 60-70° C. to afford 1.295 kg (86.65%) of I-2 which was 99.45% pure by HPLC.

Example 3

Carbonic acid (2R,3R,4R,5R)-5-(4-amino-2-oxo-2H-pyrimidin-1-yl)-4-fluoro-2-isobutoxycarbonyloxymethyl-4-methyl-tetrahydro-furan-3-yl ester isobutyl ester (I-4)

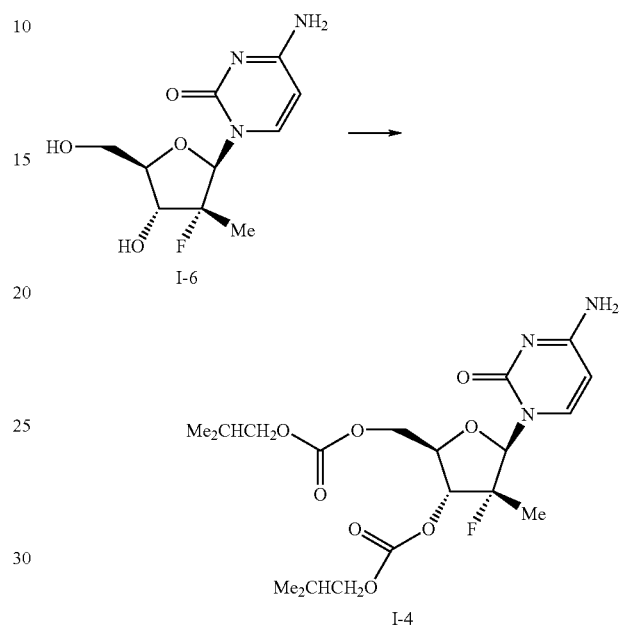

A suspension of I-6 (700 mg), DMAP (33 mg) in THF (7 mL) was diluted with brine (7 mL). Dilute NaOH was added until the pH was ca. 11. The reaction mixture was cooled in an ice bath and isobutyl chloroformate (1.11 g) is added dropwise to the stirred biphasic reaction mixture maintaining pH at about 11 by addition of NaOH as required. HPLC analysis indicated mostly dicarbonate contaminated with ca. 15% of monocarbonates. An added additional 1 eq. of isobutyl chloroformate was added dropwise to the ice-cold solution. The HPLC indicated nearly complete conversion. The resulting mixture was allowed to stand overnight at RT. EtOAc (ca. 50 mL) was added and the pH of the aqueous phase is adjusted to ca. 7.5 with con HCl. The phases were separated and the organic phase was washed with water (3×) and evaporated to dryness to afford a colorless solid (ca. 1.22 g). The solid is dissolved in hot acetone resulting in a clear solution that was slowly cooled to RT which produced a mass of solid. The solid was diluted with IPA (ca. 20 mL) which produced a slurry which was filtered then washed sequentially with IPA and heptane then dried to afford 0.85 g (68.5%) of 1-4 which was 97.5% pure by HPLC.

Example 4

Carbonic acid (2R,3R,4R,5R)-5-(4-amino-2-oxo-2H-pyrimidin-1-yl)-4-fluoro-4-methyl-2-propoxycarbonyloxymethyl-tetrahydro-furan-3-yl ester propyl ester; hydrochloride salt (I-5)

To a suspension of I-6 (700 mg, 2.70 mmol), DMAP (33 mg, 0.27 mmol) in THF (7 mL) and diluted brine (7 mL) was added dilute KOH to adjust the pH to ca. 11. The reaction was cooled to ca. 5° C. and n-propyl chloroformate (1.0 g) was added dropwise to the stirred biphasic reaction mixture. HPLC analysis indicated the formation of the desired product along with ca 20% of monocarbonates. Two additional quantities of propyl chloroformate were added (2×1 equivalent) to the cold solution until the HPLC analysis indicated the reaction had proceeded to completion. The reaction mixture was diluted with EtOAc (30 mL) and the pH of the aqueous phase is adjusted to ca. 6.5 with con HCl. The phases were separated and the organic phase is washed with water (3×) and evaporated to dryness to obtain a colorless solid (ca. 1.1 g). A hot IPA solution was acidified with 4N HCl (ca. 1 mL) and evaporated to dryness. The resulting solid was redissolved in hot EtOH (ca. 115 mL) and stirred overnight at RT. A solid mass is formed which was filtered and the residue washed with MeOH/heptane (1:1). The remaining solid was dried in vacuo at about 60° C. to afford 0.325 g (25.8%) of 1-5 which 97.5% pure by HPLC assay.

Example 5

Determination of Pharmacokinetic Parameters in Rats

Intact male IGS Wistar Han Rats Crl:WI(GLx/BRL/Han) IGS BR (Hanover-Wistar) rats weighing 200-250 g were used. Groups of three rats were used for each dose level of an experimental compound. Animals were allowed normal access to chow and water throughout the experiment. The test substance was formulated as an aqueous suspension containing Captex355EP, Capmul MCM, EtOH, and propylene glycol (30:20:20:30) at a dose equivalent to 10 mg/kg of the I-6 and was administered orally by gavage. A blood sample (0.3 mL) was collected from the treated rats at, 0.25, 0.5, 1, 3, 5, and 8 h from a jugular cannula and at 24 h by cardiac puncture. Potassium oxalate/NaF were added to the samples which were stored on ice during sampling procedure. The samples were spun in a refrigerated centrifuge at −4° C. as soon as possible and the plasma samples were stored in a −80° C. freezer until analysis. Aliquots of plasma (0.05 mL) were mixed with 0.1 mL of acetonitrile. Internal standard (0.05 mL in water) and 0.02 mL blank solvent were added. A set of calibration standards was prepared by mixing 0.05-mL aliquots of plasma from untreated rats with 0.1 mL acetonitrile, 0.02-mL aliquots of standard solution in methanol:water (1:1) and 0.05-mL aliquots of the internal standard in water. Each plasma sample and calibration standard was vortexed thoroughly and then centrifuged at 3000 rpm for 5 min to precipitate the protein. Supernatant (100 μL each) from centrifugation was transferred into a 96-well plate containing 200 μL of aqueous mobile phase for LC/MS/MS analysis.

Sample Analysis—Prodrugs were analyzed using high-performance liquid chromatography with tandem mass-spectrometry (HPLC/MS/MS). An Thermo Aquasil C18 4.6×50 mm column (5 μM) was used for separation. Electrospray Ionization (ESI) was used for the ionization process. The mobile phase A contained 5 mM ammonium acetate in water with 0.1% formic acid and mobile phase B contained MeOH with 0.1% Formic Acid. Elution was performed with the following gradient with a flow rate of 1 mL/min.:

| Time | % A | % B |
|---|---|---|
| 0 min | 95 | 5 |
| 0.5 min | 95 | 5 |
| 0.8 min | 85 | 15 |
| 1.5 min | 85 | 15 |
| 2.8 min | 10 | 90 |
| 3.8 min | 10 | 90 |
| 3.9 min | 95 | 5 |
| 5 min | 95 | 5 |

Example 6

Determination of Pharmacokinetic Parameters in Monkey

Three male Cynomolgus monkeys weighing 8-10 kg were used. Animals were allowed normal access to chow and water throughout the experiment. Animal weights at the time of drug administration and untoward reactions of the animals were recorded. The test substance was formulated as an aqueous suspension formulation containing hypromellose (2910, 50 cps), USP, polysorbate 80, NF, benzyl alcohol, NF (5.0, 4.0 and 9.0 mg/mL) and sterile water (quantity sufficient to yield 1.0 mL) at a dose equivalent to 10 mg/kg of the I-6 and 0.5 mL/kg was administered orally by gavage. A blood sample (0.5-1.0 mL) was collected at 0, 0.083, 0.25, 0.5, 1, 3, 5, 8 and 24 h. Sample handling and analysis was carried out as described in the rat experiment. A 5 mL urine sample was taken from each monkey prior to dosing and at 0-8 h. Urine samples were stored at −80° C. and analyzed by LC/MS/MS. Standard curves were prepared in blank monkey plasma containing NaF and potassium oxalate.

Example 7

Caco Protocol

Materials

Powders of Krebs-Henseleit buffer, calcium chloride dihydrate, and sodium bicarbonate were purchased from Sigma (St. Louis, Mo.). Caco-2 cells (Passage ~100) were obtained from Roche Basel. DMEM/high medium, 4-(2-hydroxyethyl)-1-piperazineethane-sulfonic acid (HEPES), and bovine serum were obtained from JRH Bioscience (Lenexa, Kans.). MEM nonessential amino acids, L-glutamine, penicillin, and streptomycin were obtained from GIBCO Labs, Life Tech. LLC (Grand Island, N.Y.). Snapwell cell culture inserts (6.5 mm diameter, 1.12 cm$^2$, 0.4 μm pore size) were obtained from Costar (Cambridge, Mass.).

Cell Cultures

Cells were grown in 75-cm$^2$ flasks and maintained at 37° C. in an atmosphere of 5% $CO_2$ and 95% air. Culture media consisted of DMEM/high medium supplemented with 5% bovine serum, 25 mM HEPES, 1% MEM non-essential amino acids, 1% L-glutamine, 100 U/mL penicillin, and 100 μg/mL streptomycin. Cultures were passaged every week at a split ratio of 1-3. For the permeability studies, Caco-2 cells at passage number 110-120 were plated at a density of 400,000 cells/cm$^2$ on Transwell polycarbonate filters in Snapwell inserts and allowed to culture for 7 days prior to use.

Krebs-Henseleit Buffer

Krebs-Henseleit bicarbonate buffer containing 10 mM glucose and 2.5 mM $CaCl_2$ adjusted to pH 6.5 and 7.4 were prepared per packet instructions. Powder salts were quantitatively dissolved in about 90% of required volume with Millipore water. Calcium chloride dihydrate and sodium bicarbonate were added before pH adjustment with 1N HCl or 1N NaOH. Additional Millipore water was added to bring the solution to final volume. The solution was sterilized by filtration using membrane with a porosity of 0.22 microns and stored in the refrigerator (~20° C.) until use.

Cell Preparation

Differentiated cells were obtained from Cell Culture Core Facility and allowed to equilibrate at 37° C. in an atmosphere of 5% $CO_2$ and 95% air. Snapwells inserts, containing caco-2 monolayers were rinsed in 37° C. equilibrated Krebs-Henseleit pH 7.4 buffer.

Method

The cell insert was utilized as the diffusion chamber. The pH of the Krebs-Henseleit buffer in the apical and basolateral chambers was 6.5 and 7.4, respectively, and the initial concentration of substrate in apical side was 100 μM. The cells with tested compound in apical chamber were pre-incubated for approximately 30 minutes at 37° C. under an atmosphere of 5% $CO_2$ and 95% air. The experiments were initiated when the cell inserts with 100 μM compounds in pH 6.5 Krebs-Henseleit buffer were transferred into a new plate with pre-equilibrated buffer in basolateral chamber. Samples from donor side at 0 minute, and both donor and receiver sides at 30 minutes were collected for analysis.

Post-Experiment Control

Lucifer Yellow was used to assess the performance of the diffusion system. Following the last sampling for test compounds, Lucifer Yellow was added to the apical chamber to give an initial concentration of 100 μM. After 60 minutes of incubation, 250 μL was removed from the basal chamber and assayed.

Calculation of Permeability Coefficient ($P_{app}$)

The $P_{app}$ was calculated using the following formula:

$$P_{app} = \frac{V \times dC}{A \times C_o \times dt} = (cm/sec)$$

Where V is the volume ($cm^3$) of the receiver solution, A is the surface area ($cm^2$) of the Snapwell insert, $C_o$ is the initial concentration (nM), and dC/dt is the change in concentration in the receiver chamber over time, i.e., the slope (nM/min) of the concentration in the receiver chamber vs. time. Concentrations at each sampling time point were corrected to account for the aliquots removed or transferring of donor inserts to new plates depending on the experiment.

Example 8

Pharmaceutical compositions of the subject compounds for administration via several routes were prepared as described in Example 8.

| Composition for wet granular formulation for oral administration (A) | |
|---|---|
| Ingredient | % wt./wt. |
| Intragranular | |
| Active ingredient (I-2) | 50.0 |
| Mannitol (Partech M200) USP | 39.0 |
| Povidone K30 USP | 5.0 |

| Composition for wet granular formulation for oral administration (A) | |
|---|---|
| Ingredient | % wt./wt. |
| Croscarmellose sodium NF | 4.0 |
| Purified water USP | for granulation |
| Extragranular | |
| Croscarmellose USP | 2.0 |

The ingredients are mixed, granulated and dispensed into hard gelatin capsules containing about 500 mg of active compound

| Composition for Oral Administration (B) | |
|---|---|
| Ingredient | % wt./wt. |
| Active ingredient (I-2) | 50.0 |
| Mannitol (Partech M200)USP | 30.0 |
| Povidone K30 USP | 5.0 |
| Croscarmellose sodium NF | 9.5 |
| Microcrystalline cellulose | 5.0 |
| Magnesium stearate | 0.5 |

The ingredients are combined and granulated using a solvent such as water. The formulation is then dried and formed into tablets containing about 500 mg of active compound with an appropriate tablet machine.

| Composition for Oral Administration (C) | | |
|---|---|---|
| Ingredient | % wt./wt. | |
| Active compound | 6 | g |
| Carboxymethylcellulose | 1 | g |
| Methyl paraben | 0.15 | g |
| Propyl paraben | 0.05 | g |
| Flavoring | 0.035 | mL |
| Colorings | 0.5 | mg |
| Distilled water | q.s. to 100 | mL |
| Hydrochloric Acid | q.s. to adjust ca. pH 4 | |

The ingredients are mixed to form a suspension for oral administration.

| Suppository Formulation (D) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and

We claim:

1. A compound of formula I

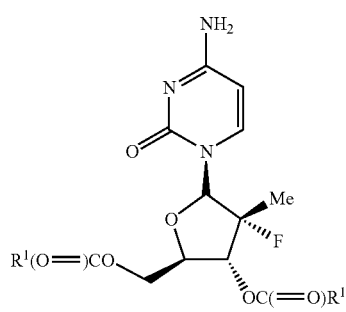

wherein:
R¹ is selected from the group consisting of $C_{2-5}$ unbranched or branched alkyl, $C_{2-5}$ unbranched or branched alkenyl, $C_{2-5}$ unbranched or branched alkynyl, $C_{2-5}$ lower haloalkyl, $C_{3-6}$ cycloalkyl, and $C_{2-4}$ alkoxy; and,
acid addition salts thereof.

2. A compound according to claim 1 wherein R¹ is ethyl, n-propyl, iso-propyl, n-butyl or iso-butyl.

3. A compound according to claim 2 wherein R¹ is ethyl or iso-propyl.

4. A compound according to claim 3 wherein R¹ is iso-propyl and the compound is the hydrochloride or sulfate salt.

5. A compound according to claim 1 wherein R¹ is ethoxy, n-propyloxy or iso-propyloxy.

6. A method for treating a disease mediated by the Hepatitis C Virus (HCV) virus comprising administering to a mammal in need thereof, a therapeutically effective quantity of a compound according to claim 1.

7. The method of claim 6 wherein the compound a dose of between 0.1 and 10 g per day is administered to the patient.

8. A method according to claim 7 wherein a dose of between 0.5 and 7.5 g per day is administered to the patient.

9. A method according to claim 7 wherein a dose of between 1.0 and 6.0 g per day is administered to the patient.

10. The method of claim 6 further comprising administering at least one immune system modulator and/or at least one antiviral agent that inhibits replication of HCV.

11. The method of claim 10 wherein the immune system modulator is an interferon, interleukin, tumor necrosis factor or colony stimulating factor.

12. The method of claim 11 wherein the immune system modulator is an interferon or chemically derivatized interferon.

13. The method of claim 10 further comprising administering at least one other antiviral agent.

14. The method of claim 13 where the antiviral compound is selected from the group consisting of an HCV protease inhibitor, another nucleoside HCV polymerase inhibitor, a non-nucleoside HCV polymerase inhibitor, an HCV helicase inhibitor, an HCV primase inhibitor and an HCV fusion inhibitor.

15. A pharmaceutical composition comprising a therapeutically effective quantity of a compound according to claim 1 admixed with at least one pharmaceutically acceptable carrier, diluent or excipient.

16. A process for the selective O-acylation of a nucleoside II to afford an O-acyl nucleoside I under basic reaction conditions

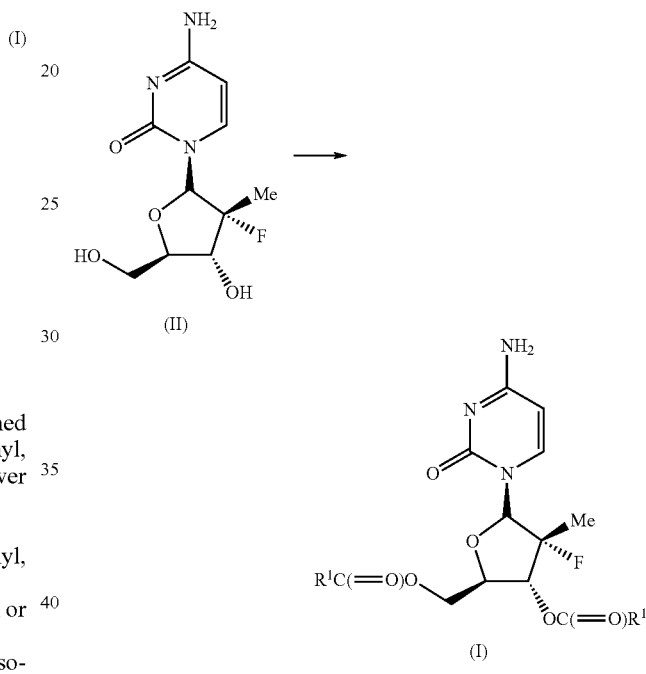

wherein R¹ is selected from the group consisting of $C_{2-5}$ unbranched or branched alkyl, $C_{2-5}$ unbranched or branched alkenyl, $C_{2-5}$ unbranched or branched alkynyl, $C_{2-5}$ lower haloalkyl, $C_{3-6}$ cycloalkyl, and $C_{2-4}$ alkoxy which process comprises the steps of:

(i) dissolving II and DMAP in a heterogeneous aqueous solvent mixture and adding aqueous base to adjust the pH from about 7.5 to about 12;

(ii) optionally adding sufficient saturated aqueous NaCl to produce a biphasic reaction mixture;

(iii) adding an acylating agent and additional base sufficient to maintain the pH from about 7.5 to about 12;

(iv) monitoring the reaction and discontinuing addition of said acylating agent and said base when the conversion reaches a satisfactory level;

(v) optionally contacting the O-acyl nucleoside with a pharmaceutically acceptable acid to form an acid additional salt of the O-acyl nucleoside.

* * * * *